(12) United States Patent
Vona, Jr.

(10) Patent No.: US 8,058,246 B2
(45) Date of Patent: Nov. 15, 2011

(54) METHOD AND COMPOSITION TO ACHIEVE STABLE COLOR OF ARTIFICIALLY COLORED HAIR

(75) Inventor: Samuel A. Vona, Jr., Bound Brook, NJ (US)

(73) Assignee: Akzo Nobel N.V., Arnhem (NL)

( * ) Notice: Subject to any disclaimer, the term of this patent is extended or adjusted under 35 U.S.C. 154(b) by 1420 days.

(21) Appl. No.: 10/789,004

(22) Filed: Feb. 27, 2004

(65) Prior Publication Data

US 2005/0188481 A1  Sep. 1, 2005

(51) Int. Cl.
*A61K 31/00* (2006.01)
(52) U.S. Cl. ............................ 514/23; 424/401; 424/70.1
(58) Field of Classification Search .................... None
See application file for complete search history.

(56) References Cited

U.S. PATENT DOCUMENTS

| | | | |
|---|---|---|---|
| 4,465,702 | A | 8/1984 | Eastman et al. |
| 4,477,480 | A | 10/1984 | Seidel et al. |
| 5,037,929 | A | 8/1991 | Rajagopalan et al. |
| 5,131,953 | A | 7/1992 | Kasica et al. |
| 5,149,799 | A | 9/1992 | Rubens |
| 5,187,272 | A | 2/1993 | Katcher et al. |
| 5,674,478 | A | 10/1997 | Dodd et al. |
| 5,750,122 | A | 5/1998 | Evans et al. |
| 5,871,756 | A | 2/1999 | Jeffcoat et al. |
| 5,906,822 | A | 5/1999 | Samour et al. |
| 5,911,980 | A | 6/1999 | Samour et al. |
| 6,344,183 | B2 * | 2/2002 | Paul et al. ................. 424/47 |
| 6,365,140 | B1 * | 4/2002 | Melby et al. ............... 424/70.1 |
| 2002/0194684 | A1 | 12/2002 | Wiesche et al. |
| 2003/0028978 | A1 | 2/2003 | Wiesche et al. |
| 2003/0033678 | A1 | 2/2003 | Wiesche et al. |

FOREIGN PATENT DOCUMENTS

| | | | |
|---|---|---|---|
| EP | 0 469 232 | | 2/1992 |
| EP | 0469232 | A1 | 2/1992 |
| EP | 0829255 | A2 | 4/1992 |
| EP | 0469232 | A1 * | 6/1992 |
| EP | 0 509 922 | | 10/1992 |
| EP | 0 554 818 | A2 | 8/1993 |
| EP | 0 829 255 | | 3/1998 |
| EP | 0829255 | * | 3/1998 |
| EP | 0829255 | A2 * | 3/1998 |
| EP | 1 166 745 | | 1/2002 |
| EP | 1166745 | A1 | 1/2002 |
| GB | 1 285 547 | | 8/1972 |
| GB | 1285547 | * | 8/1972 |
| GB | 1285547 | A | 8/1972 |
| JP | 6 206809 | | 7/1994 |
| JP | 11 349450 | | 12/1999 |
| JP | 2003 231619 | | 8/2003 |
| WO | WO 95/04082 | | 2/1995 |
| WO | 9622073 | A2 | 7/1996 |
| WO | WO 96/22073 | | 7/1996 |

OTHER PUBLICATIONS

Wuzburg; "Modified Starches: Their Chemistry and Properties," Section 1, CRC Press, Inc., Florida, pp. 3-196 (1986).
Chapter XXII—Production and Uses of Pregelatinized Starch, Starch: Chemistry and Technology, vol. III, Industrial Aspects, R.L. Whistler et al., New York (1967).

* cited by examiner

*Primary Examiner* — Anand Desai
*Assistant Examiner* — Melissa Mercier
(74) *Attorney, Agent, or Firm* — Norris McLaughlin & Marcus, P.A.

(57) ABSTRACT

The present invention relates to a composition comprising at least one amylose-containing starch, and its use in extending or improving the color durability and stability of artificially colored hair. Such compositions may be applied either as a leave-on or as a rinse-off composition.

17 Claims, No Drawings

METHOD AND COMPOSITION TO ACHIEVE STABLE COLOR OF ARTIFICIALLY COLORED HAIR

BACKGROUND OF THE INVENTION

The present invention relates to a composition, which extends the stability of artificially colored hair and a method of achieving such extended color stability. Such composition comprises at least one amylose containing starch.

A significant segment of the global population uses products to change the natural color of their hair. This segment continues to grow at a substantial rate. Hair color products are typically classified into three categories: permanent, semi-permanent, and temporary. They may either be applied directly by the consumer, or by a hair care professional.

Unfortunately, despite manufacturers' claims that their hair color products result in hair color which remains constant throughout the entire period the hair remains on the head, it is well recognized by consumers that artificially colored hair color may fade or change dramatically over time. The biggest problem recognized in the hair color industry is maintaining the vibrancy and durability of artificially colored red hair.

Hair color is hypothesized to fade or change during normal hair treatment such as washing and styling, particularly by exposure to solvents, such as water and ethanol. Exposure to the environment, such as light, may also play a part in hair color fading.

Many approaches have been tried to improve the durability and stability of hair color. These include changes to hair color formulations, pre-shampoo treatments, and additives to conditioners.

Surprisingly, it has now been found that compositions comprising at least one amylose-containing starch have use in extending or improving the color durability and stability of artificially colored hair. Such compositions may be applied either as a leave-on or as a rinse-off composition.

SUMMARY OF THE INVENTION

The present invention relates to a composition comprising at least one amylose-containing starch, and its use in extending or improving the color durability and stability of artificially colored hair. Such compositions may be applied either as a leave-on or as a rinse-off composition.

As used herein, the term "leave-on" is intended to mean a composition that is applied to and left on the hair for at least one hour until the next cleansing.

As used herein, the term "rinse-off" is intended to mean a composition that is applied to the hair and washed therefrom shortly after application.

As used herein, the term "amylose containing" is intended to include all normal starches as well as high amylose starches, the amylose portion of fractioned starches and debranched waxy starches.

DETAILED DESCRIPTION OF THE INVENTION

The present invention relates to a composition comprising at least one amylose-containing starch, and its use in extending or improving the color durability and stability of artificial hair coloring agents. Such compositions may be applied either as a leave-on or as a rinse-off composition.

Starch, as used herein, is intended to include all starches derived from a native source, any of which may be suitable for use herein. A native starch as used herein, is one as it is found in nature. Also suitable are starches derived from a plant obtained by standard breeding techniques including cross-breeding, translocation, inversion, transformation or any other method of gene or chromosome engineering to include variations thereof. In addition, starch derived from a plant grown from artificial mutations and variations of the above generic composition, which may be produced by known standard methods of mutation breeding, are also suitable herein.

Typical sources for the starches are cereals, tubers, roots, legumes and fruits. The native source can be corn, pea, potato, sweet potato, banana, barley, wheat, rice, sago, amaranth, tapioca, arrowroot, canna, sorghum, and high amylose varieties thereof. As used herein, the term "high amylose" is intended to include a starch containing at least about 50%, more particularly at least 70%, most particularly at least about 80%, by weight amylose. The amylose portions of fractionated starches are also suitable.

Starch consists of two types of $\alpha$-D-glucose polymers: amylose and amylopectin. The amylose component is linear or nearly linear containing very few branching points. The amylose molecular weight typically varies from $10^5$ to $10^6$, though it may vary depending upon variety. The amylopectin component is a highly branched molecule, whose molecular weight typically varies from $10^7$ to $10^8$.

Waxy varieties of the above may also be used as a base starch. The term waxy starch, as used herein, is intended to include a starch containing no more than about 10%, particularly no more than about 5%, more particularly no more than about 3%, and most particularly no more than about 1% amylose by weight.

Such starches must be debranched using methods known in the art so that the resulting starch material is significantly linear, particularly at least 60%, more particularly at least 70% linear, by number of chains. The chain length of the debranched material must also remain at an average degree of polymerization of at least about 10, preferably at least about 15, more particularly at least about 20.

Debranching may be achieved by any method known in the art, particularly by use of an enzyme capable of cleaving the alpha-1,6-linkages of the starch. Particularly suitable enzymes include endo-alpha-1,6-D-glucanohydrolases, particularly pullulanase and isoamylase.

The starch may be modified using any modification known in the art, including physical, chemical and/or enzymatic modifications, to achieve the desired properties and functionality.

Physically modified starches, such as sheared starches, or thermally-inhibited starches described in the family of patents represented by WO 95/04082, may be suitable for use herein.

Chemically modified products are also suitable and include, without limitation, those that have been crosslinked, acetylated and organically esterified, hydroxyethylated and hydroxypropylated, phosphorylated and inorganically esterified. Also suitable are cationic, anionic, nonionic, and zwitterionic, and succinate and substituted succinate derivatives thereof. Such modifications are known in the art, for example in *Modified Starches: Properties and Uses*, Ed. Wurzburg, CRC Press, Inc., Florida (1986).

Conversion products derived from any of the starches, including fluidity or thin-boiling starches prepared by oxidation, enzyme conversion, acid hydrolysis, heat and or acid dextrinization, thermal and or sheared products may also be useful herein.

The amylose containing starch must be gelatinized prior to application. Particularly suitable are pregelatinized starches, which are known in the art and disclosed for example in U.S. Pat. Nos. 4,465,702, 5,037,929, 5,131,953, and 5,149,799.

Conventional procedures for pregelatinizing starch are also known to those skilled in the art and described for example in Chapter XXII— "Production and Use of Pregelatinized Starch", *Starch: Chemistry and Technology*, Vol. III—Industrial Aspects, R. L. Whistler and E. F. Paschall, Editors, Academic Press, New York 1967. Alternatively, the starch can be heated until gelatinization occurs prior to use in the composition.

Any starch or starch blend having suitable properties for use herein may be purified by any method known in the art to remove starch off notes and colors, which are native to the polysaccharide or created during processing. Suitable purification processes for treating starches are disclosed in the family of patents represented by EP 554 818 (Kasica, et al.). Alkali washing techniques, for starches intended for use in either granular or pregelatinized form, are also useful and described in the family of patents represented by U.S. Pat. No. 4,477,480 (Seidel) and U.S. Pat. No. 5,187,272 (Bertalan et al.) as well as bleaching processes.

Particularly suitable starches are high amylose starches, cationic amylose-containing starches, and pregelatinized amylose-containing starches.

The starch component may be a single starch, a blend of modified starches, or a blend of modified and native starches. Blends may be particularly useful to lower the cost of the composition or to more easily achieve a variety of desirable properties and functionalities.

Typically, the amylose-containing starch will be applied to the hair either in a leave-on composition or as a rinse-off composition. The composition may be in any form known in the art including with limitation as a mousse, gel, pomade, wax, aerosol or other spray, emulsion or liquid. The composition may be applied as part of the normal hair regime or may be added specifically to protect the artificial color of the hair. Such compositions may contain a variety of other components known in the art and have additional functionality, such as styling.

Optional components may be added for a variety of reasons including without limitation, to style and/or condition the hair. Such optional components include, without limitation, antioxidants, conditioners, styling agents, polymers, emollients, humectants, and moisturizers, aesthetic enhancers, emulsifiers and surfactants, thickeners, UV protectors, and viscosifying agents, waxes, resins, gums, softening agents, foaming agents, propellants, preservatives, silicones, and perfumes (fragrances).

Particularly suitable conditioning agents can include but are not limited to individual polyquaternium compounds and blends of them and other conditioning agents. Examples of suitable polyquaternium compounds included Polyquaternium-4 and Polyquaternium-10.

Particularly suitable styling agents can include but are not limited to styling polymers and other styling ingredients typically used in all types of styling products such as mousses, gels, aerosol hair sprays, non-aerosol hair sprays, pomades, waxes, etc.

Such styling polymers may include, but are not limited to, the following polymers used individually or as blends: corn starch modified, octylacrylamide/acrylates/butaminoethyl methacrylate copolymer, acrylate/octylacrylamide copolymer, acrylates copolymer, sodium polystyrene sulfonate, VA/crotonates/vinyl neodecanoate copolymer, and polyurethane-14 (and) amp-acrylates copolymer.

Such optional components are typically added in minor amounts, particularly less than about 30% total by weight based upon the weight of the starch component. The only limitation on the optional ingredients is that the composition remain compatible and safe for use on hair or other keratin fibers.

The starch is typically used in amounts ranging from about 0.25 to about 10 percent, particularly from about 0.5 to about 5 percent, more particularly from about 1 to 3 percent, by weight of the composition. It may be added to the composition using any of the techniques known in the art including simple addition with or without the other components to water, or by heating to cook out the starch if not pregelatinized.

The amylose-containing starch composition is added to the dyed hair using methods conventional in the art. The composition is applied to the dyed hair in the form of a solution or dispersion (ie. not in dry form). Such composition may be, without limitation, in the form of oily or alcohol-based lotions, emulsions, and aqueous or water-alcohol dispersions, particularly an aqueous dispersion.

If applied in a rinse-off composition, the composition may be applied shortly before shampooing, or after the shampooing processing, such as during the conditioning processing. The rinse-off composition is rinsed out shortly after application. Rinse-off compositions would include, without limitation, pre-shampoo treatments, cream rinses and conditioners. A particularly suitable rinse-off conditioner is one which is applied shortly before, and is allowed to dry prior to, shampooing.

In contrast, a leave-on composition is applied during some other time period, typically during the normal hair regime. The leave-on composition is not rinsed out of the hair shortly after application and typically will remain in the hair until the next shampoo.

The amylose-containing starch composition may also be applied to other dyed keratin fibers to protect it from color degradation. Such fibers include natural and synthetic fibers using in a variety of applications known in the art such as fabric and carpeting.

The amylose-containing starch composition is applied in an amount effective to stabilize artificial color on hair such that its color remains true for a longer period of time.

EXAMPLES

The following examples are presented to further illustrate and explain the present invention and should not be taken as limiting in any regard. All percents used are on a weight/weight basis.

Example 1

Methodology to Detect Color Fading

Ten inch long hair swatches approximately 1 inch wide containing 4.5 grams of European medium brown hair that had been bleached one time and permanent waved (straight) were employed throughout. These hair swatches were colored with a commercial hair coloring kit offering "permanent" hair coloring according to the directions contained within the kit.

One of these hair swatches was dried and kept as is after following the directions of the color kit (0 wash). One of these hair swatches was subject to 3 cleansing cycles (3 wash). One of these hair swatches was subject to 5 cleansing cycles (5 wash). One of these hair swatches was subject to 7 cleansing cycles (7 wash). One of these hair swatches was subject to 10 cleansing cycles (10 wash). These five swatches comprise what will be referred to as the spectrum of color fading in that they demonstrate a spectrum of color resulting from the cleansing induced fading over the course of 10 successive cleansing cycles.

A cleansing cycle is defined as follows. A swatch is rinsed for 30 seconds under running tap water at approximately 5.67 liters/minute and between 35 and 38° C. One mL of Prell Shampoo is applied to the swatch and massaged into the hair for 15 seconds. The swatch is then rinsed for an additional 30 seconds under tap water. The swatch is then hung and allowed to dry.

Hair swatches were treated with L'Oreal® Superior Preference® Permanent Color Kit (RR06) or with Schwarzkopf Professional Igora 4-88. Panelists were presented with a pair of swatches and asked to determine if there was a difference in the degree of 'redness' of the pair. Each permutation of swatch pairs was presented to the panelists.

Eight panelists were employed for each pairing and the pairings were presented to the panelists in random order. The following table describes the results of the study.

| Swatch with x number of cleansing cycles compared to swatch with y number of cleansing cycles (x/y) | # of 8 Panelists choosing x as more red than y (Schwarzkopf Professional Igora 4-88) | # of 8 Panelists choosing x as more red than y (L'Oreal ® Superior Preference ® RR06) |
|---|---|---|
| 0/3 | 8 | 8 |
| 0/5 | Not tested | 8 |
| 0/7 | 8 | 8 |
| 0/10 | Not tested | 8 |
| 3/5 | Not tested | 8 |
| 3/7 | 8 | 8 |
| 3/10 | 8 | 8 |
| 5/7 | 8 | 8 |
| 5/10 | 8 | 8 |
| 7/10 | Not tested | 8 |

This table demonstrates that panelists can detect cleansing induced color fading in the form of less red color over the course of successive cleansing cycles. This is consistent with consumer experience with hair coloring kits. It also demonstrates that panelists can discriminate between the color fading caused by 3 cleansing cycles on color treated hair.

When testing the benefit of a color protection polymer an additional step is added to the cleansing cycle. In the case of the polymer incorporated into a leave-on product, an additional step is added to apply the leave-on product and allow it to dry before cleansing. In the case of the polymer incorporated into a rinse-off conditioner product, the following additional steps are added to the cleansing cycle. 1 mL of a rinse-off conditioner is applied to the hair swatch and massaged in for 15 seconds. The hair swatch is then rinsed for 30 seconds before drying. Hair swatches used to test the benefit of a color protection polymer are subject to 10 cleansing cycles. These swatches will be referred to as test swatches.

At the end of these ten cleansing cycles, panelists are presented with the swatches comprising the spectrum of color fading and asked to determine which swatch in the spectrum of color fading most closely approximates the color of the test swatch. This methodology allows statements such as the following. Using a leave-on product containing "Polymer #1" between each cleansing cycle, over the course of 10 cleansing cycles, shows the fading normally observed after only 3 cleansing cycles without using the leave-on product containing "Polymer #1".

In this respect the lower # of cleansing cycles corresponds to greater color protection.

Example 2

Leave-on Product Preparation

The following example demonstrates the preparation of non-aerosol hair sprays used to evaluate the benefits of various polymers used in a leave-on application. Additional ingredients such as sunscreens (e.g. octyl methoxy cinnamate, benzophenone-3, etc) and antioxidants (e.g. ascorbic acid) could be added to this formula to protect against photo-induced color fading as well.

Two grams of polymer were dispersed in 49 grams of water. In those cases where the polymer was not readily cold-water-dispersible, the polymer was dispersed by heating the water to 90 C and adding the polymer with mixing for 30 minutes. Forty-nine grams of ethanol were added to the cool aqueous polymer dispersion with mixing. The resulting mixture was introduced into a standard non-aerosol hair spray container fitted with a standard non-aerosol hair spray valve and actuator. The following table lists the various polymers that were employed. A non-aerosol hair spray made according to this process was prepared for each polymer.

| Id # | Polymer | Polymer Composition |
|---|---|---|
| LO1 | Corn starch modified | Amylose/Amylopectin |
| LO2 | Polyquaternium-4/Hydroxy propyl starch phosphate | Amylose/Amylopectin |
| LO3 | Cationic corn starch | Amylose/Amylopectin |
| LO4 | Cationically modified corn starch | Amylose/Amylopectin |
| LO5 | Hydrophobically modified corn starch | Amylose/Amylopectin |
| LO6 | Corn Starch | Amylose/Amylopectin |
| LO7 | CWS agglomerated corn starch | Amylose/Amylopectin |
| LO8 | Enzyme debranched waxy maize starch | Short Chain Amylose |
| LO9 | Potato Starch | Amylose/Amylopectin |
| LO10 | CWS corn starch | Amylose/Amylopectin |
| LO11 | Hydroxy propyl starch phosphate | Amylopectin |
| LO12 | Waxy Maize | Amylopectin |
| LO13 | Polyquaternium-16 | Cationic Acrylate |
| LO14 | Polyquaternium-16 | Cationic Acrylate |
| LO15 | Polyquaternium-4 | Cationic Hydroxethylcellulose |
| LO16 | Polyquaternium-4 | Cationic Hydroxyethylcellulose |
| LO17 | Octylacrylamie/acrylates/butylamino ethyl methacrylate copolymer | Acrylates copolymer |
| LO18 | Polyurethane-14 and AMP Acrylates Copolymer | Acrylate and polyurethane |
| LO19 | Sodium Polystyrene Sulfonate | Sodium Polystyrene Sulfonate |
| LO20 | No Polymer | — |

Example 3

Rinse-off Conditioner Preparation

The following table lists the ingredients found in the standard rinse-off conditioner prototype used to test for hair color protection benefits of various polymers. Additional ingredients such as sunscreens (e.g. octyl methoxy cinnamate, benzophenone-3, etc) and antioxidants (e.g. ascorbic acid) could be added to this formula to protect against photo-induced color fading as well.

| Ingredient | Level |
| --- | --- |
| Water | QS |
| EDTA | 0.15 |
| Amodimethicone (and) Tallowtrimonium Chloride (and) Nonoxynol-10 | 3 |
| Butylene glycol | 3 |
| Glycerin | 2 |
| Hexadecyltrimethylammonium chloride (25%) | 3.5 |
| Cetearyl alcohol | 2 |
| Dimethicone (100 cst) | 1 |
| Cyclomethicone | 3 |
| Dimethicone Copolyol | 1 |
| Acryloyldimethyltaurate/Beheneth-25 Methacrylate Crosspolymer | 0.5 |
| Polymer (solids) | 2 |

Water, polymer (when present), EDTA, Amodimethicone (and) Tallowtrimonium Chloride (and) Nonoxynol-10, butylene glycol, glycerin, and Hexadecyltrimethylammonium chloride (25%) were combined and heated to 90° C. to form phase A. Cetearyl alcohol, Dimethicone copolyol, and Cyclomethicone 100 cst were combined and heated to 90° C. to form phase B.

Phase B was slowly added to Phase A with mixing. The material was then allowed to cool to 50° C. and DC345 was added with mixing. Finally, Acryloyldimethyltaurate/Beheneth-25 Methacrylate Crosspolymer was added and thoroughly dispersed.

Emulsions prepared in this way gave rheology consistent with typical rinse-off conditioner products.

The following polymers were incorporated into rinse-off conditioners.

| ID # | Polymer | Polymer Composition |
| --- | --- | --- |
| RO1 | Corn starch modified | Amylose/Amylopectin |
| RO2 | Polyquaternium-4/Hydroxy propyl starch | Amylose/Amylopectin |
| RO3 | Cationic corn starch | Amylose/Amylopectin |
| RO4 | Cationically modified corn starch | Amylose/Amylopectin |
| RO5 | Exp 3 | Amylose/Amylopectin |
| RO6 | CWS agglomerated corn starch | Amylose/Amylopectin |
| RO7 | CWS corn starch | Amylose/Amylopectin |
| RO8 | Hydroxy propyl starch phosphate | Amylopectin |
| RO9 | No polymer | — |

Example 4

Evaluation of Leave on Products for Hair Color Protection Benefits

Leave-on non-aerosol hair sprays were tested for their color protection benefits according to the method described in Example 1. Three complete bursts from the non-aerosol pump were applied to each side of the swatch.

For each leave-on product, the results of 8 panelist's evaluations are presented in the table below. An (*) next to the ID # indicates results observed for both the L'Oreal® and Schwarzkopf products whereas no (*) indicates results only for the Schwarzkopft product. The columns represent the # swatch in the spectrum of color fading described in example 1. The number in each cell corresponds to the number of panelists that believed that the test swatch's color, after 10 leave-on treatment/cleansing cycles, most closely matched the color of that swatch from the spectrum of color fading. For example, all eight panelists believed that hair swatches treated with LO1 and cleansed ten times showed the color fading observed after 5 cleansing cycles without leave-on treatment.

| Id # | Polymer | Polymer Composition | 0 | 3 | 5 | 7 | 10 |
| --- | --- | --- | --- | --- | --- | --- | --- |
| LO1* | Corn starch modified | Amylose/Amylopectin | | | 8 | | |
| LO2* | Polyquaternium-4/Hydroxy propyl starch phosphate | Amylose/Amylopectin | | 1 | 6 | 1 | |
| LO3* | Cationic corn starch | Amylose/Amylopectin | | 1 | 7 | | |
| LO4* | Cationically modified corn starch | Amylose/Amylopectin | | 6 | 2 | | |
| LO5 | Hydrophobically modified corn starch | Amylose/Amylopectin | | 1 | 6 | 1 | |
| LO6 | Corn Starch | Amylose/Amylopectin | | | 6 | 2 | |
| LO7* | CWS agglomerated corn starch | Amylose/Amylopectin | | | 8 | | |
| LO8 | Enzyme debranched waxy maize starch | Amylose | | | 4 | 4 | |
| LO9 | Potato Starch | Amylose/Amylopectin | | | 6 | 2 | |
| LO10* | CWS corn starch | Amylose/Amylopectin | | 6 | 2 | | |
| LO11* | Hydroxy propyl starch phosphate | Amylopectin | | | | | 8 |
| LO12 | Waxy Maize | Amylopectin | | | | | 8 |
| LO13* | Polyquaternium-16 | Cationic Acrylate | | | | | 8 |
| LO14 | Polyquaternium-16 | Cationic Acrylate | | | | | 8 |
| LO15* | Polyquaternium-4 | Cationic Hydroxyethyl-cellulose | | | | | 8 |
| LO16 | Polyquaternium-4 | Cationic Hydroxyethyl-cellulose | | | | | 8 |
| LO17 | Octylacrylamie/acrylates/butylaminoethyl methacrylate copolymer | Acrylates copolymer | | | | | 8 |
| LO18 | Polyurethane-14 and AMP Acryaltes Copolymer | Acrylate and polyurethane | | | | | 8 |
| LO19* | Sodium Polystyrene Sulfonate | Sodium Polystyrene Sulfonate | | | | | 8 |
| LO20* | No Polymer | — | | | | | 8 |

Leave-on products with a greater population of panelists selecting lower numbers indicates better performance in protecting hair color.

First, these data demonstrate that the ethanol/water solution representing the leave-on with no polymer provided no color protection benefit whatsoever (LO20). The data show that the color fading is observed for different permanent hair color products. Furthermore, it demonstrates that polymers can provide color protection benefits when delivered from a leave-on product (LO1-LO10).

Also, the data shows that of those tested, only starch polymers can provide that benefit (LO1-LO10). Finally, it is a criticality that the starch polymer contain amylose (LO1-LO10 compared to LO11-LO12).

Example 5

Evaluation of Rinse Off Products for Hair Color Protection Benefits

Rinse-off conditioners were tested for their color protection benefits according to the method described in Example 1.

For each rinse-off conditioner, the results of 8 panelist's evaluations are presented in the table below. An (*) next to the ID # indicates results observed for both the L'Oreal and Schwarzkopf products whereas no (*) indicates results only for the Schwarzkopft product. The columns represent the # swatch in the spectrum of color fading described in example 1. The number in each cell corresponds to the number of panelists that believed that the test swatch's color, after 10 conditioner treatment/cleansing cycles, most closely matched the color of that swatch from the spectrum of color fading. For example, all eight panelists believed that hair swatches treated with RO1 and cleansed ten times showed the color fading observed after 5 cleansing cycles without conditioner treatment.

| Id # | Polymer | Polymer Composition | 0 | 3 | 5 | 7 | 10 |
|---|---|---|---|---|---|---|---|
| RO1* | Corn starch modified | Amylose/Amylopectin | | | 8 | | |
| RO2 | Polyquaternium-4/Hydroxy propyl starch | Amylose/Amylopectin | | | 6 | 2 | |
| RO3 | Cationic corn starch | Amylose/Amylopectin | | | 7 | 1 | |
| RO4 | Cationically modified corn starch | Amylose/Amylopectin | | | 2 | 6 | |
| RO5 | Corn Starch | Amylose/Amylopectin | | | 1 | 7 | |
| RO6* | CWS agglomerated corn starch | Amylose/Amylopectin | | | 7 | 1 | |
| RO7* | CWS corn starch | Amylose/Amylopectin | | 1 | 7 | | |
| RO8* | Hydroxy propyl starch phosphate | Amylopectin | | | | 6 | 2 |
| RO9 | CWS corn starch (0.5%) | Amylose/Amylopectin | | | 2 | 5 | 1 |
| RO10 | CWS corn starch (3%) | Amylose/Amylopectin | | 1 | 7 | | |
| RO11 | No polymer | — | | | | 7 | 1 |

First, these data demonstrate that the conditioner base, itself, (RO11) shows some color protection benefits. The data show that the effect is observed for different permanent hair color products. Furthermore, it demonstrates that polymers can enhance color protection benefits of rinse-off products (RO1-RO8). Also, the data demonstrates that it is a criticality that the starch polymer must contain some level of amylose (RO1-RO7 compared to RO8). Finally, the data demonstrates that best color protection benefits are achieved with amylose containing starch polymers at a concentration greater than about 0.5%.

I claim:

1. A method of improving the color durability and stability of artificial color on hair comprising:
    applying to artificially colored hair a composition comprising a pregelatinized amylose-containing starch; and
    allowing the pregelatinized starch to dry prior to shampooing.

2. The method according to claim 1 wherein the pregelatinized amylose-containing starch is a modified starch.

3. The method according to claim 2 wherein the modified starch is at least cationically modified starch.

4. The method according to claim 2 wherein the modified starch is at least nonionically modified starch.

5. The method according to claim 1 wherein the pregelatinized amylose-containing starch is pregelatinized corn starch.

6. The method according to claim 1 wherein the pregelatinized amylose-containing starch is present in an amount of from about 0.25 to about 10% by weight, based on total weight of the composition.

7. The method according to claim 1 wherein the composition is a leave-in composition or a rinse-off composition.

8. The method according to claim 6 wherein the composition is a rinse-off composition and the rinse-off composition is at least a pre-shampoo treatment.

9. The method according to claim 1 wherein the composition is selected from mousse, gels, pomades, waxes, hair sprays, conditioners, and mixtures thereof.

10. The method according to claim 1 wherein the composition further comprises a hair fixative.

11. The method according to claim 1 wherein the pregelatinized amylose-containing starch is high amylose-containing starch.

12. The method according to claim 11 wherein the high amylose-containing starch comprises at least about 50% by weight, based on total weight of the starch, of amylose.

13. The method according to claim 1 wherein the composition further comprises a polyquaternium compound.

14. The method of claim 13 wherein the polyquaternium compound is cationic hydroxyethylcellulose.

15. The method of claim 13 wherein the polyquaternium compound is cationic acrylate.

16. The method according to claim 1 wherein the composition further comprises a blend of quaternium compounds.

17. The method according to claim 4 wherein the nonionically modified starch is hydroxypropyl starch.

* * * * *